US 6,728,570 B2

(12) United States Patent
Kim (10) Patent No.: US 6,728,570 B2
(45) Date of Patent: Apr. 27, 2004

(54) RADIO FREQUENCY COIL FOR MAGNETIC RESONANCE IMAGE

(75) Inventor: Ho T. Kim, Suwon-si (KR)

(73) Assignee: Dong Bo Systems Co., Ltd., Kunpo (KR)

( * ) Notice: Subject to any disclaimer, the term of this patent is extended or adjusted under 35 U.S.C. 154(b) by 195 days.

(21) Appl. No.: 10/001,723

(22) Filed: Oct. 31, 2001

(65) Prior Publication Data

US 2002/0055677 A1 May 9, 2002

(30) Foreign Application Priority Data

Nov. 7, 2000 (KR) .................................. 2000-0065949

(51) Int. Cl.[7] ............................................. A61B 5/055
(52) U.S. Cl. ...................... 600/422; 324/318; 324/322; 5/601
(58) Field of Search ................................ 600/421, 422, 600/411, 415; 324/307, 309, 316, 318, 322; 5/601; 343/718, 741–751

(56) References Cited

U.S. PATENT DOCUMENTS

| 5,261,403 A | * | 11/1993 | Saito et al. ................. 600/422 |
| 5,351,688 A | * | 10/1994 | Jones .......................... 600/422 |
| 5,361,765 A | * | 11/1994 | Herlihy et al. .............. 600/422 |
| 5,390,672 A | * | 2/1995 | Jones .......................... 600/422 |
| 5,450,091 A | * | 9/1995 | Hama .......................... 343/718 |
| 5,477,146 A | * | 12/1995 | Jones .......................... 324/318 |
| 6,438,402 B1 | * | 8/2002 | Hashoian et al. ........... 600/410 |

* cited by examiner

Primary Examiner—Eleni Mantis Mercader
(74) Attorney, Agent, or Firm—Park & Sutton LLP; John K. Park (57) ABSTRACT

A radio frequency coil for a magnetic resonance image apparatus includes a first support frame provided with a first coil, a second support frame opposing the first support frame and provided with a second coil, a gap adjuster for adjusting a gap between the first and second support frames according to the size of a specimen, and a frequency sustainer for sustaining a resonance frequency set according to change of the gap. The magnetic resonance image apparatus adopting the radio frequency coil alleviates impatience of a patient, to thereby enable rejection of patients with respect to the magnetic resonance image apparatus to be solved. Also, the magnetic resonance image apparatus enables a patient to be imaged and during operation. In addition, the second support frame can be moved to reduce a gap between the first and second support frames to thereby greatly improve quality of an image.

4 Claims, 7 Drawing Sheets

RADIO FREQUENCY COIL FOR MAGNETIC RESONANCE IMAGE

CLAIMING FOREIGN PRIORITY

The applicant claims and requests a foreign priority, through the Paris Convention for the Protection of Industry Property, based on a patent application filed in the Republic of Korea (South Korea) with the filing date of Nov. 7, 2000, with the patent application number 2000-0065949, by the applicant.

BACKGROUND OF THE INVENTION

1. Field of the Invention

The present invention relates to a radio frequency coil for a magnetic resonance image apparatus being a medical diagnostic apparatus for grasping the internal structure of a specimen such as a patient, and more particularly, to a radio frequency coil for a magnetic resonance image apparatus which can adjust a gap between support frames for supporting a specimen according to the physical structure of the specimen.

2. Description of the Related Art

There are an X-ray CT (Computer Tomography) using an X-ray and a MRI (Magnetic Resonance Image) using a magnetic signal of an element in a human body as tomographies for grasping the internal structure of a human body. A tomography using a magnetic resonance phenomenon has some advantages in comparison with a tomography of an X-ray CT. The tomography using a magnetic resonance phenomenon uses a magnetic field which does no harm to a human body, which is thus not harmful even in the case of long-time and frequent tomographic diagnosis, and can discriminate particles which has not been discriminated in the case of an X-ray tomography. Also, the magnetic resonance tomography can obtain a two-dimensional or three-dimensional tomographic image in any direction of X-, Y- and Z-axis (or any three-dimensional direction) and at any position. With the above-described merits, the MRI equipment has become an essential medical image apparatus.

The MRI equipment includes a main magnet, a coil and a scan processor. The main magnet is a permanent magnet, an electromagnet or a superconductive magnet using a superconductor, in order to form a strong magnetic filed, in which the intensity of the magnetic filed ranges from 0.2 Tesla to 7.0 Tesla. Here, one Tesla is a magnetic filed of ten thousand gauss. The coil includes a slant magnetic coil for forming a slant magnetic filed of X-, Y- and Z-axis directions, a transmission radio frequency (RF) coil for giving energy to an atomic nucleus spin in a human body of a patient and forming a magnetic resonance signal and a reception radio frequency (RF) coil for receiving the magnetic resonance signal emitted from the human body which is a specimen. The scan processor includes a spectrometer for demodulating the received magnetic resonance signal and amplifying it, a controller for controlling operation of each coil, and a processor for performing a Fourier transform operation in order to transform the received signal into data on the XY plane.

Figure 1:
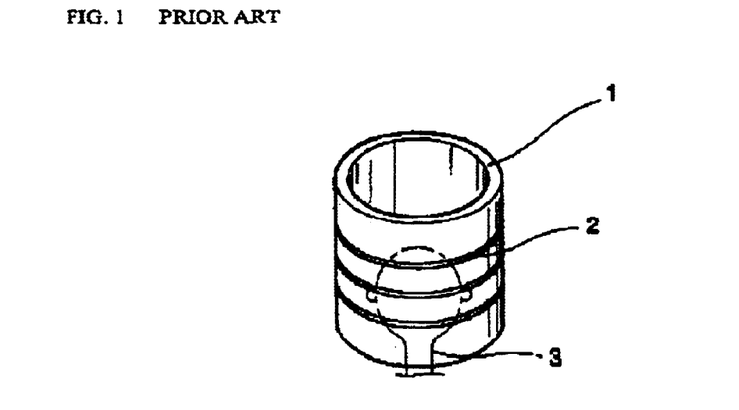
FIG. 1 is a view showing a conventional radio frequency coil for a magnetic resonance image apparatus.

An example of a magnetic resonance image apparatus having the above-described elements is shown in FIG. 1, which has a structure that a three-turn coil 2 is disposed on a cylindrical support frame 1 with an equal interval, in which a specimen 3 is inserted into the cylindrical support frame 1.

In a conventional magnetic resonance image apparatus, the cylindrical support frame 1 has a closed structure. As a result, a patient is easy to feel impatience during a photographic action of a tomography and a rejection against the magnetic resonance image apparatus. Further, since the cylindrical support frame has a predetermined limited space, it is difficult to perform an accurate tomography in the case that a patient is tall or small in a physical size. That is, in the case that a physical size of a patient is large, equipment of a variety of sizes is needed according to the size of the patient. In the case that a physical size of a patient is small, a quality of an image is lowered since a patient is distant from the magnetic resonance image apparatus and it takes much time to take a photograph since a patient moves frequently.

SUMMARY OF THE INVENTION

To solve the above problems, it is an object of the present invention to provide a radio frequency coil for a magnetic resonance image apparatus, for solving a rejection against a magnetic resonance image apparatus by reducing impatience of a patient during photography, adjusting a gap between a patient and a magnetic resonance image apparatus according to the size of a patient, receiving a signal having a less loss by facilitating a close contact between the patient and the magnetic resonance image apparatus, to thereby obtain an enhanced image, and shortening a photographic time efficiently by minimizing movement of the patient through a close contact of the patient.

To accomplish the above object of the present invention, there is provided a radio frequency coil for a magnetic resonance image apparatus comprising: a first support frame provided with a first coil; a second support frame opposing the first support frame and provided with a second coil; a gap adjuster for adjusting a gap between the first and second support frames according to the size of a specimen; and a frequency sustainer for sustaining a resonance frequency set according to change of the gap in the gap adjuster.

Preferably, the first support frame is fixedly installed on a base and the second support frame is slidably installed on the base. Preferably, the gap adjuster comprises: a pair of first guide bars fixedly installed on the lower portion of the first support frame with a predetermined distance from each other, and formed in the lengthy direction of the second support frame; a second guide bar fixedly installed on the lower portion of the second support frame and combined between the pair of the first guide bars slidably; and a first guide rail provided on the base, for guiding the second support frame.

The frequency sustainer comprises: a first cylindrical electrode electrically connected to the first coil, fixed on the first support frame, and formed in the lengthy direction of the gap adjustment, in which an opening is formed in an outer circumferential surface so that a surface area increases gradually; and a second cylindrical electrode electrically connected to the second coil, fixed to the second support frame, and combined with the first coil slidably in which an insulator is interposed between the first cylindrical electrode and the second cylindrical electrode, to thereby increase or decrease capacitance values of the first and second cylindrical electrodes according to adjustment of the gap between the first and second support frames when reactance values of the first and second coils increase or decrease.

The radio frequency coil for a magnetic resonance image apparatus can adjust a gap according to the physical size of a patient since the gap between the first and second support frames can be adjusted.

BRIEF DESCRIPTION OF THE DRAWINGS

The above object and other advantages of the present invention will become more apparent by describing the preferred embodiments thereof in more detail with reference to the accompanying drawings in which.

PREFERRED EMBODIMENTS OF THE INVENTION

A radio frequency coil for a magnetic resonance image apparatus according to a preferred embodiment of the present invention will be described below with reference to the accompanying drawings.

Figure 2:
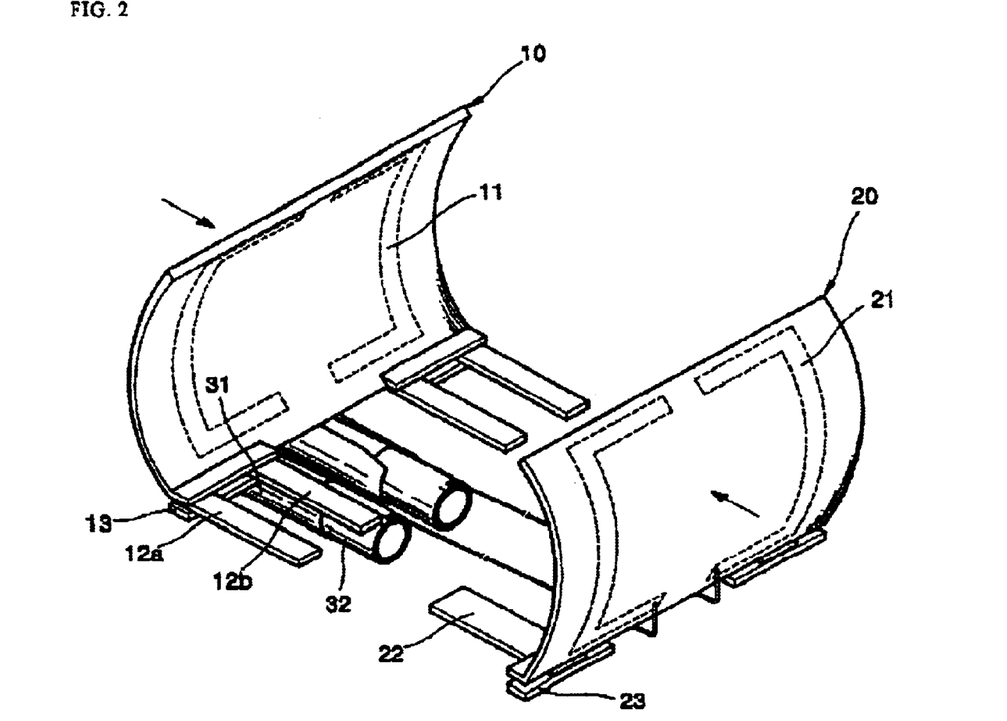
FIG. 2 is an exploded perspective view showing a radio frequency coil for a magnetic resonance image apparatus according to the present invention.
Figure 3:
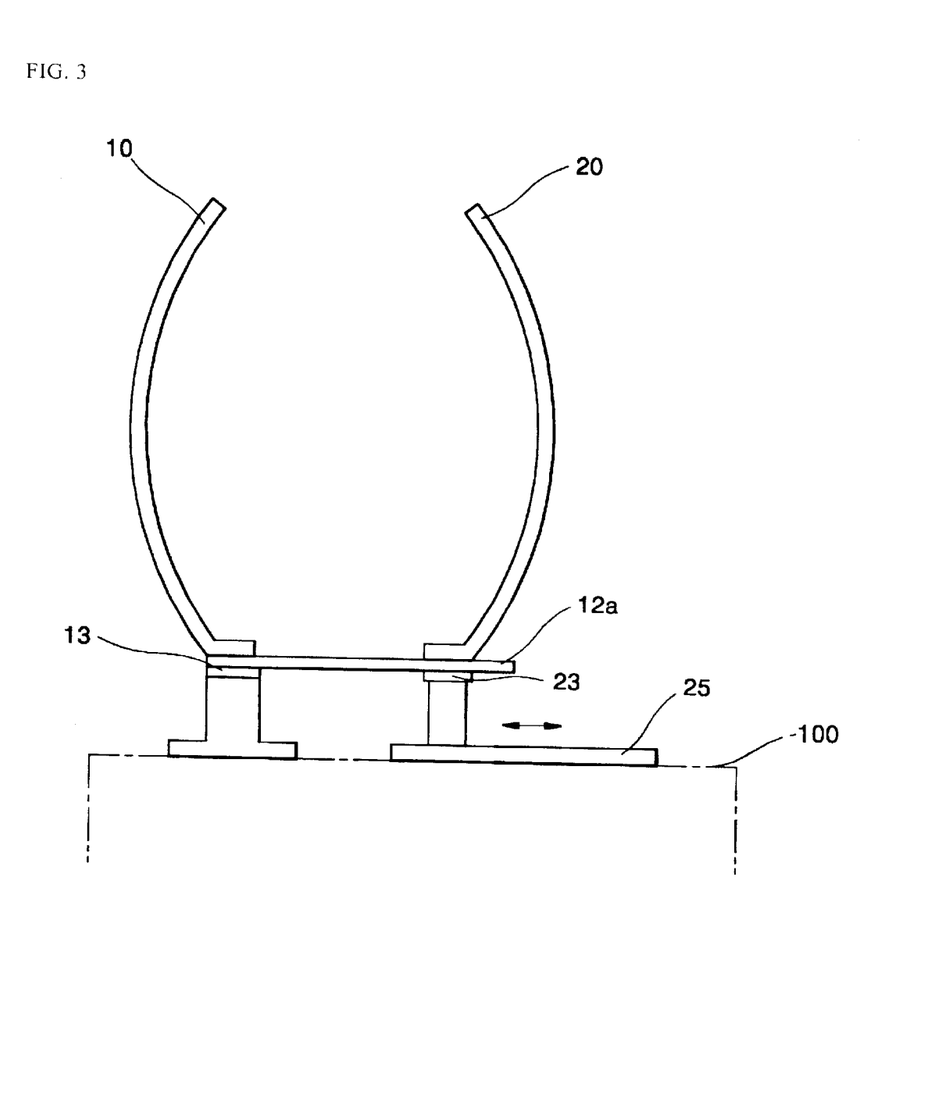
FIG. 3 is a side view for explaining a gap adjuster employed in a radio frequency coil for a magnetic resonance image apparatus according to the present invention.
Figure 4A:
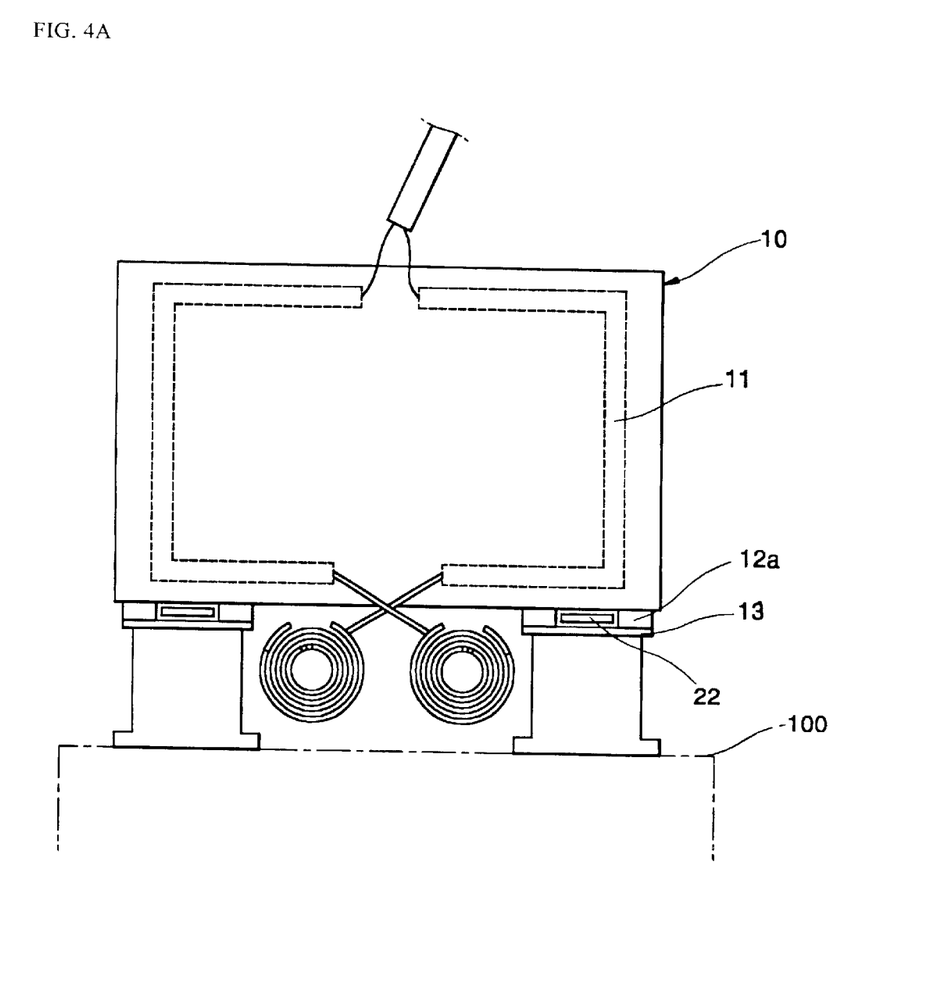
FIG. 4A is a side view showing the radio frequency coil for a magnetic resonance image apparatus of FIG. 2, which is taken along a direction of "a"
Figure 4B:
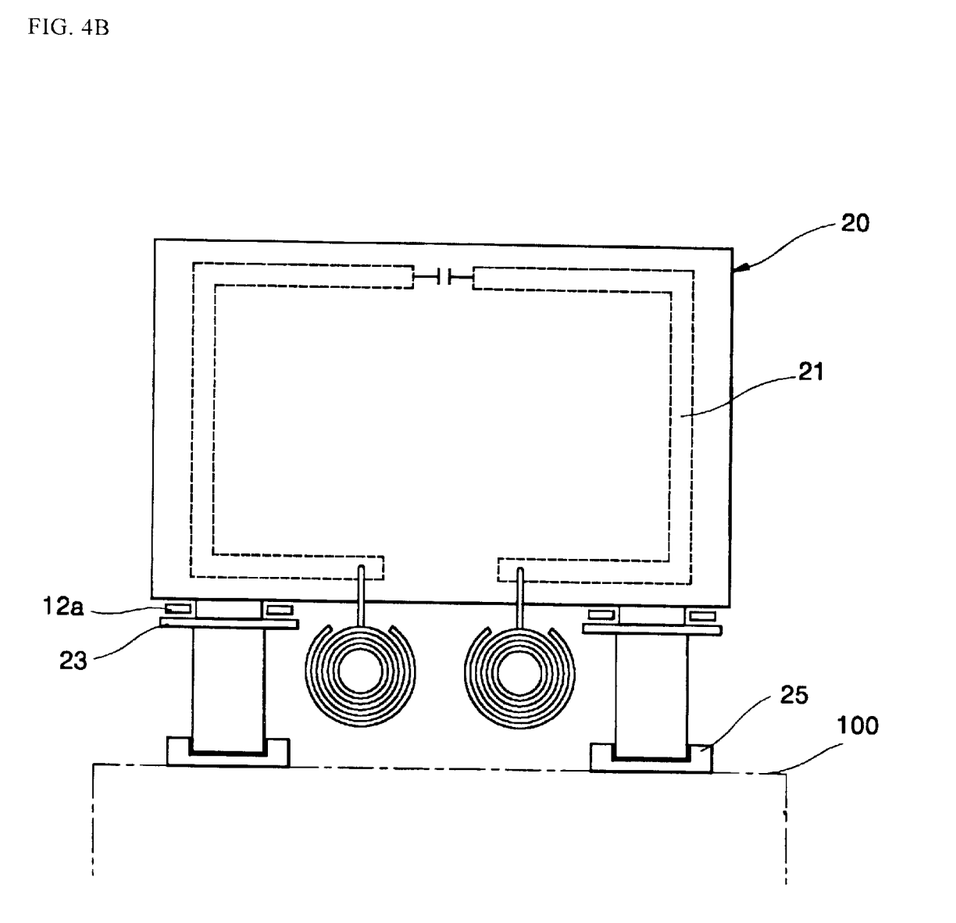
FIG. 4B is a side view showing the radio frequency coil for a magnetic resonance image apparatus of FIG. 2, which is taken along a direction of "b"

Referring to FIG. 2, a radio frequency coil for a magnetic resonance image apparatus according to the present invention, includes a first support frame 10 provided with a first coil 11 of a predetermined pattern, a second support frame 20 opposing the first support frame 10 and provided with a second coil 21 of a predetermined pattern, a gap adjuster for adjusting a gap between the first and second support frames 10 and 20 according to the size of a specimen or a patient, and a frequency sustainer for sustaining a resonance frequency set according to change of the gap in the gap adjuster.

The first and second support frames 10 and 20 are formed as semi-cylindrical structures, and made of a non-magnetic material such as acryl, plastic or FRP having a non-conductivity. Each support frame 10 or 20 is preferably formed of a transparent material so that a patient can be observed from the outside of the magnetic resonance image apparatus.

The first and second coils 11 and 21 are made of high frequency materials, that is, a copper plate, in which coil patterns are formed along the edges of the first and second support frames 10 and 20. The coil patterns are provided with a structure that C-shaped copper plates are mutually opposingly arranged on the first and second support frames 10 and 20.

Meanwhile, referring to FIGS. 2 through 4B, the first support frame 10 is fixedly installed on a base 100 and the second support frame 20 is slidably installed on the base 100. In the gap adjuster, a pair of first guide bars 12a and 12b are fixedly installed on the lower portion of the first support frame 10 with a predetermined distance from each other, and formed in the lengthy direction of the second support frame 20. A second guide bar 22 is fixedly installed on the lower portion of the second support frame 20 and combined between the pair of the first guide bars 12a and 12b slidably. The first and second guide bars 12a and 12b and 22 are provided on both sides of the support frames 10 and 20, respectively. Also, a first guide rail 25 is provided on the base 100, for guiding the second support frame 20.

Meanwhile, referring to FIGS. 2, and 4 through 6, the frequency sustainer includes a first cylindrical electrode 31 electrically connected to the first coil 11, fixed on the first support frame 10, and formed in the lengthy direction of the gap adjustment, in which an opening 31a is formed in an outer circumferential surface so that a surface area increases gradually, and a second cylindrical electrode 32 electrically connected to the second coil 21, fixed to the second support frame 20, and combined with the first coil 31 slidably in which insulators 34 and 35 are interposed between the first cylindrical electrode 31 and the second cylindrical electrode 32. Accordingly, the frequency sustainer has a structure of increasing or decreasing capacitance values of the first and second cylindrical electrodes 31 and 32 according to adjustment of the gap between the first and second support frames 10 and 20 when reactance values of the first and second coils 11 and 21 increase or decrease.

Figure 5:
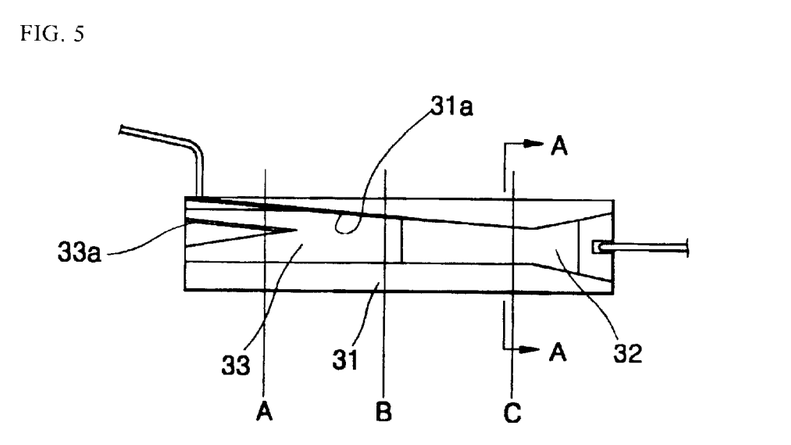
FIG. 5 is a schematic view for explaining an electrode structure employed in a frequency sustainer which is adopted in a radio frequency coil for a magnetic resonance image apparatus.

By an equation of $\omega=1/(2\pi\times\sqrt{LC})$ in which $\omega$ indicates a resonance frequency, L indicates a reactance and C indicates a capacitance, a value of L and a value of C are inversely proportional with each other. By an equation of $C=\epsilon\times A/d$ in which $\epsilon$ indicates a dielectric of an insulator, A indicates an area of an electrode, and d indicates a distance between the electrodes, a value of C increases in proportional with an area of an electrode. Thus, when a distance between the two support frames 10 and 20 is larger, that is, a gap between the first and second coils 11 and 21 is wider, if a coil reactance value decreases, the second electrode 32 moves together with the second support frame 20. In other words, as shown in FIG. 5, the second electrode 32 moves from an "A" position to a "C" position, and thus moves in the direction where a surface area of the first electrode 31 gradually increases, to thereby bring about an increase of a value of C, that is, a capacitance value. As a result, although the gap between the first and second support frames 10 and 20 have been adjusted, a preset resonance frequency value can be maintained consistently.

Figure 6:
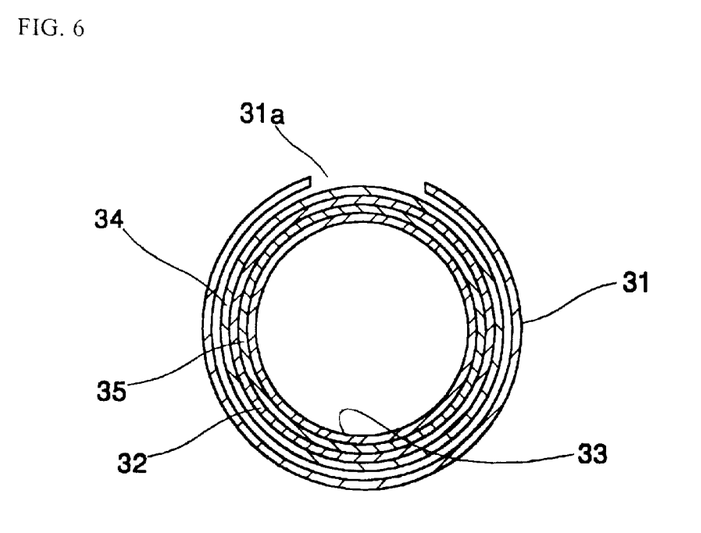
FIG. 6 is a sectional view cut along a line "A—A" of FIG. 5.

Meanwhile, the frequency sustainer further includes a third electrode 33 coaxially combined with the first electrode 31 and the second electrode 32, and mutually electrically connected to the first electrode 31 in which a notch 33a is formed in correspondence to a surface area minimal portion of the first electrode 31. In this case, when the second electrode 32 is positioned at an end of the first electrode 31, that is, at a surface are a minimal portion, a mutual interference between reactance and capacitance can be alleviated.

Figure 7:
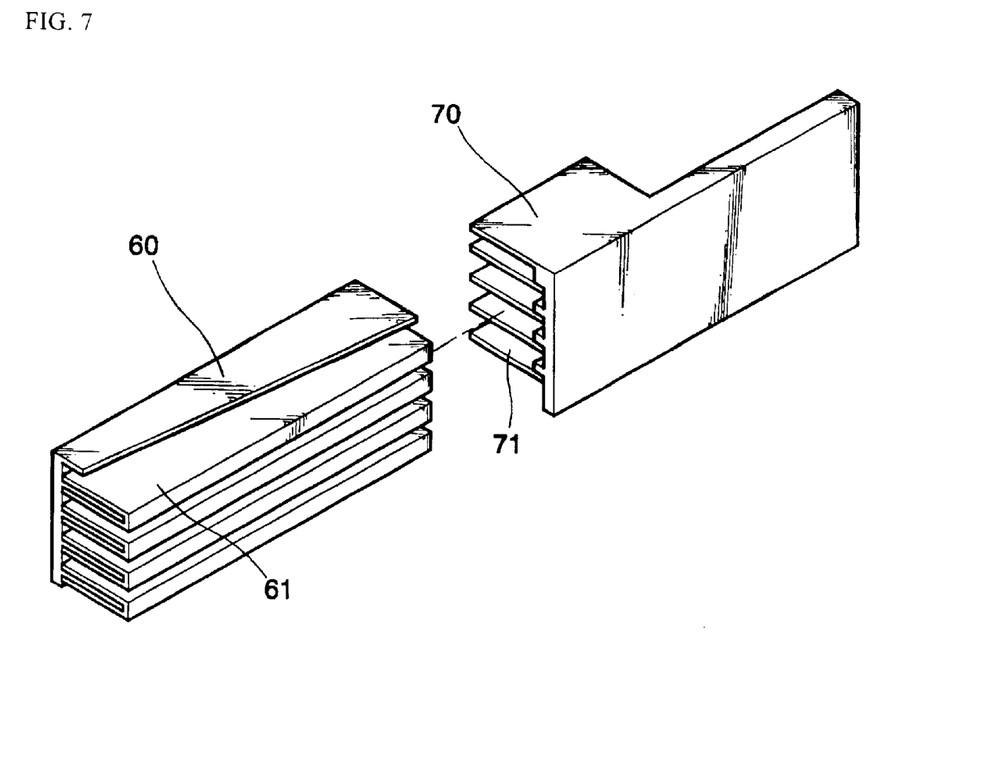
FIG. 7 is a perspective view for explaining another electrode structure employed in a frequency sustainer which is adopted in a radio frequency coil for a magnetic resonance image apparatus.
Figure 8:
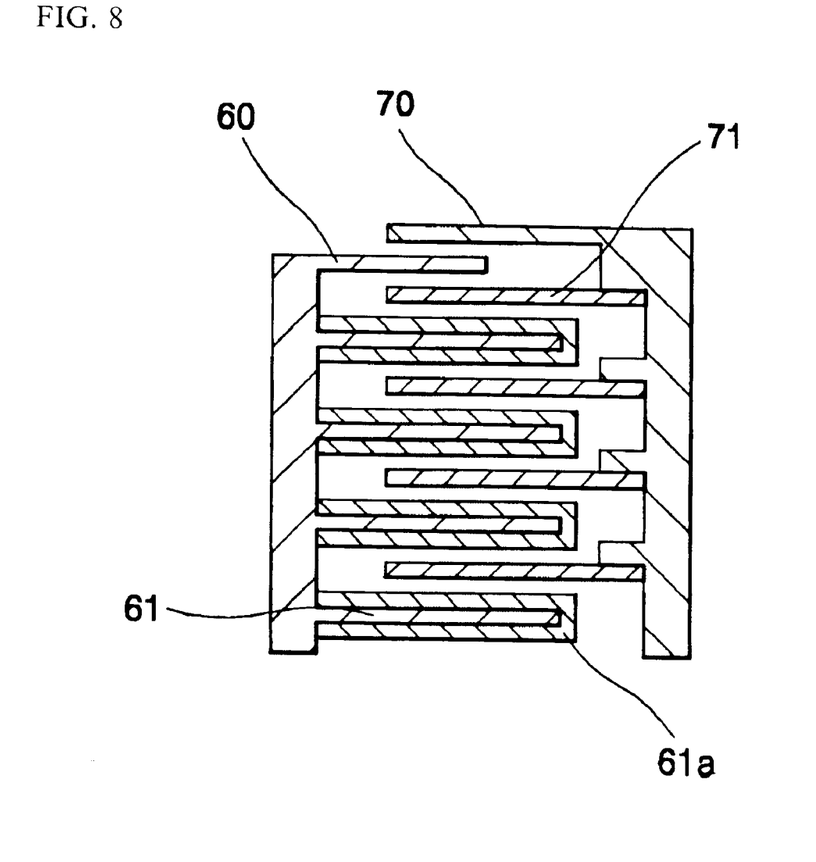
FIG. 8 is a sectional view of the combined electrode structure of FIG. 7.

Referring to FIGS. 7 and 8, another embodiment of the frequency sustainer includes a slant electrode 60 electrically connected to the first coil 11, and fixedly installed on the first support frame 10, in which a surface area gradually increases, a plate electrode 70 electrically connected to the second coil 21, fixedly installed on the second support frame 20, and opposed to the slant electrode 60 in which an insulator 61a is interposed between the slant and plate electrodes 60 and 70. Accordingly, the frequency sustainer has a structure of increasing or decreasing capacitance values of the slant and plate electrodes 60 and 70 according to adjustment of the gap between the first and second support frames 10 and 20 when reactance values of the first and second coils 11 and 21 increase or decrease. Here, since a gap adjuster for adjusting a gap between the two support frames 10 and 20 can be implemented in the same manner as that of the above-described first embodiment, the detailed description thereof will be omitted.

Meanwhile, the frequency sustainer further includes a plurality of fixed electrodes 61 electrically connected to the slant electrode 60 and overlappingly deposited in sequence with a mutually constant distance, and a plurality of movable electrodes 71 electrically connected to the plate electrode 70 and overlappingly deposited in sequence with a mutually constant distance so that the plurality of movable electrodes are disposed between the plurality of fixed electrodes 61 with a face-to-face opposing relationship, to thereby make capacitance in parallel.

Figure 9:
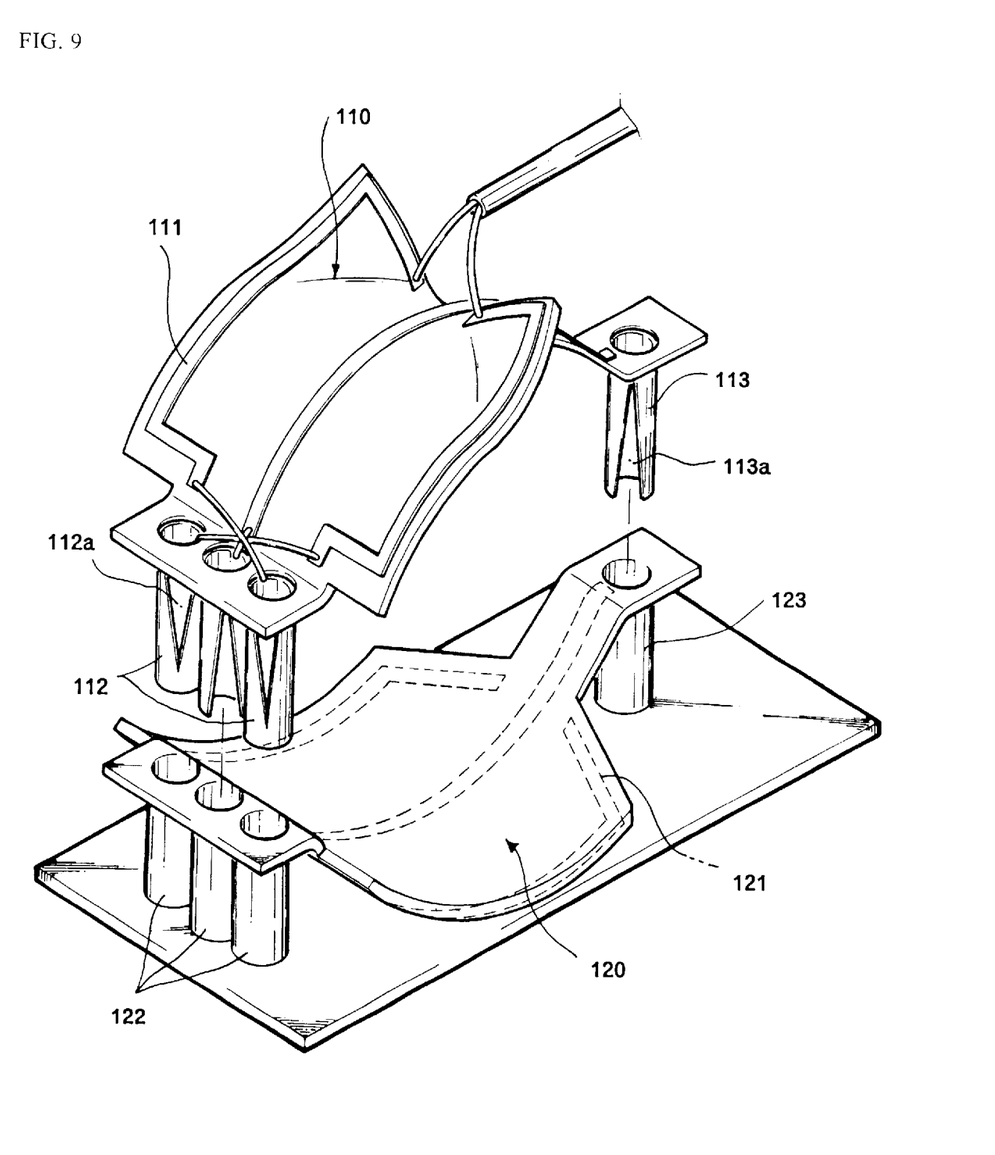
FIG. 9 is a schematic perspective view showing another embodiment of a radio frequency coil for a magnetic resonance image apparatus.

FIG. 9 is a schematic perspective view showing another embodiment of a radio frequency coil for a magnetic resonance image apparatus. In the case of the FIG. 2 embodiment, a gap adjustment is performed left and right, while in the case of the FIG. 9 embodiment, the former is performed up and down.

Referring to FIG. 9, in a magnetic resonance image apparatus according to another embodiment of the present invention, a frequency sustainer includes first cylindrical electrodes 112 and 113 electrically connected to a first coil 111, fixed on a first support frame 110 and formed in the lengthy direction of the gap adjustment in which openings 112a and 113a are formed in an outer circumferential surface so that a surface area increases gradually, and second cylindrical electrodes 122 and 123 electrically connected to a second coil 121 whose pattern is formed on the second support frame 120, and fixed to a second support frame 120, in which an insulator is interposed between the first and cylindrical electrodes, so that the first electrodes 112 and 113 are slidably combined with each other, to thereby increase or decrease capacitance values of the first and second cylindrical electrodes 112, 113 and 122 according to adjustment of the gap between the first and second support frames 110 and 120 when reactance values of the first and second coils 111 and 121 increase or decrease.

In the radio frequency coil for a magnetic resonance image apparatus as described above, part of the human body of a patient such as a head, a chest, an arm or a leg is inserted and imaged. In this case, the second support frame 20 is adjusted as a gap adjuster according to the physical size of the human body in a patient, thereby smoothing insertion of the human body. In particular, when a head portion of the human body in a patient is intended to be imaged, a physical operation of the imaged portion is possible at the same time of imaging.

The radio frequency coil for a magnetic resonance image apparatus according to the present invention is not limited in the above-described embodiments. It is apparent to one who is skilled in the art that there are many variations and modifications. For example, although the internal structure of the magnetic resonance image apparatus is schematically shown in the description and FIG. 2, a loader for supporting a specimen or a patient can be provided. Further, although it has been described that the second support frame 20 moves in the embodiment of the gap adjuster, the two support frames 10 and 20 can be designed to move together in order to adjust a gap therebetween.

As described above, a radio frequency coil for a magnetic resonance image apparatus according to the present invention solves a rejection against a magnetic resonance image apparatus by reducing impatience of a patient during imaging since the upper portions of first and second support frames are opened, adjusts a gap between a patient and a magnetic resonance image apparatus according to the size of a patient since a second support frame can move by means of the gap adjuster, receives a signal having a less loss by facilitating a close contact between the patient and the magnetic resonance image apparatus, to thereby obtain an enhanced image, and shortens a photographic time efficiently by minimizing discretionarily movement of the patient through a close contact of the patient.

What is claimed is:

1. A radio frequency coil for a magnetic resonance image apparatus comprising:

a first support frame provided with a first coil of a predetermined pattern, wherein the first support frame has a lower portion and a higher portion;

a second support frame opposing the first support frame and provided with a second coil, wherein the second support frame has a lower portion and a higher portion;

a gap adjuster for adjusting a gap between the first and second support frames according to the size of a specimen;

a frequency sustainer for sustaining a resonance frequency set according to an adjustment of the gap in the gap adjuster;

wherein said first support frame is fixedly installed on a base and the second support frame is slidably installed on the base, and wherein said gap adjuster comprises:

a pair of first guide bars fixedly installed on the lower portion of the first support frame with a predetermined distance from each other, and formed in the lengthy direction of the second support frame;

a second guide bar fixedly installed on the lower portion of the second support frame and combined between the pair of the first guide bars slidably;

and a first guide rail provided on the base, for guiding the second support frame; and wherein said frequency sustainer comprises:

a first cylindrical electrode electrically connected to the first coil, fixed on the first support frame, and formed in the lengthy direction of the gap adjustment, in which an opening is formed in an outer circumferential surface so that a surface area increases gradually; and a second cylindrical electrode electrically connected to the second coil, fixed to the second support frame, and combined with the first coil slidably in which an insulator is interposed between the first cylindrical electrode and the second cylindrical electrode, to thereby increase or decrease capacitance values of the first and second cylindrical electrodes according to adjustment of the gap between the first and second support frames when reactance values of the first and second coils increase or decrease; and wherein said frequency sustainer and said gap adjuster are at the lower portions of the first support frame and the second support frame.

2. The radio frequency coil for a magnetic resonance image apparatus of claim 1, wherein said frequency sustainer further comprises a third electrode coaxially combined with the first electrode and the second electrode, and mutually electrically connected to the first electrode in which a notch is formed in correspondence to a surface area minimal portion of the first electrode.

3. A radio frequency coil for a magnetic resonance image apparatus comprising:

a first support frame provided with a first coil of a predetermined pattern, wherein the first support frame has a lower portion and a higher portion;

a second support frame opposing the first support frame and provided with a second coil, wherein the second support frame has a lower portion and a higher portion;

a gap adjuster for adjusting a gap between the first and second support frames according to the size of a specimen;

a frequency sustainer for sustaining a resonance frequency set according to an adjustment of the gap in the gap adjuster;

wherein said first support frame is fixedly installed on a base and the second support frame is slidably installed on the base, and wherein said gap adjuster comprises:

a pair of first guide bars fixedly installed on the lower portion of the first support frame with a predetermined distance from each other, and formed in the lengthy direction of the second support frame;

a second guide bar fixedly installed on the lower portion of the second support frame and combined between the pair of the first guide bars slidably;

and a first guide rail provided on the base, for guiding the second support frame; and wherein said frequency sustainer comprises:

a slant electrode electrically connected to the first coil, and fixedly installed on the first support frame, in which a surface area gradually increases;

and a plate electrode electrically connected to the second coil, fixedly installed on the second support frame, and opposed to the slant electrode in which an insulator is interposed between the slant and plate electrodes, to thereby have a structure of increasing or decreasing capacitance values of the slant and plate electrodes according to an adjustment of the gap between the first and second support frames when reactance values of the first and second coils increase or decrease and wherein said frequency sustainer and said gap adjuster are at the lower portions of the first support frame and the second support frame.

4. The radio frequency coil for a magnetic resonance image apparatus of claim 3, wherein said frequency sustainer further comprises:

a plurality of fixed electrodes electrically connected to the slant electrode and overlappingly deposited in sequence with a mutually constant distance; and a plurality of movable electrodes electrically connected to the plate electrode and overlappingly deposited in sequence with a mutually constant distance so that the plurality of movable electrodes are disposed between the plurality of fixed electrodes with a face-to-face opposing relationship.

* * * * *